US005656592A

United States Patent [19]

Seed et al.

[11] Patent Number: 5,656,592
[45] Date of Patent: Aug. 12, 1997

[54] USE OF RELAXIN AS AN ANALGESIC AND PALLIATIVE FOR INTRACTABLE PAIN

[76] Inventors: Brian Seed, 9 Hawthorne Pl. #5J, Boston, Mass. 02114; John C. Seed, 205 Witherspoon St., Princeton, N.J. 08540

[21] Appl. No.: 128,912

[22] Filed: Sep. 29, 1993

[51] Int. Cl.$^6$ .......................... C07K 14/64; A61K 38/22
[52] U.S. Cl. ................................................ 514/12; 530/324
[58] Field of Search ............................. 514/12; 530/324

[56] References Cited

U.S. PATENT DOCUMENTS

| | | | |
|---|---|---|---|
| 4,656,249 | 4/1987 | Tregear et al. | 530/324 |
| 5,145,962 | 9/1992 | Hudson et al. | 530/324 |
| 5,179,195 | 1/1993 | Hudson et al. | 530/324 |

OTHER PUBLICATIONS

Horowitz, J.D. Am. J. Cardiology, vol. 70 Sep. 24, 1992 pp. 648–7113.
Prnewswire, Apr. 25, 1983, Abstract.
Genentech. Co. Report Oct. 14, 1987 Abstract.
Kakouris et al., Tips, vol. 181, 1306–1312 (1993).
Genentech, Inc. Anoul Report, 1992.
St. Louis et al., Life Science, vol. 37, pp. 1351–1357 (1985).
MacLennan, Scand. J. Rheumatol., Suppl. 88:7–15 (1991).
Ackland J.F. et al.; "Nonsteroidal Signals Originating in the Gonads"; *Physiological Reviews*; 72:731, 741–743 (1992).
Bryant–Greenwood G.D.; "At the Cutting Edge: The Human Relaxins: Consensus and Dissent"; *Molecular and Cellular Endocrinology*; 79:C125–C132 (1991).
Calguneri M. et al.; "Changes in Joint Laxity Occurring During Pregnancy"; *Annals of the Rheumatic Diseases*; 41:126–128 (1982).
Haley J. et al.; "Porcine Relaxin: Molecular Cloning and cDNA Structure"; *DNA*; 1:154–162 (1982).
Hudson P. et al; "Molecular Cloning and Characterization of cDNA Sequences Coding for Rat Relaxin"; *Nature*; 291:127–131 (1981).

Hudson P. et al; "Relaxin Gene Expression in Human Ovaries and the Predicted Structure of a Human Preprorelaxin by Analysis of cDNA Clones"; *The EMBO Journal*; 3:2333–2339 (1984).
Hudson P. et al.; "Structure of a Genomic Clone Encoding Biologically Active Human Relaxin"; *Nature*; 301:628–631 (1983).
Jones S.A. et al.; "Relaxin Increases Blood Pressure and Vasopressin Levels in Anaesthetized Rats"; *Physiological Society*; 37p (1986).
Kakouris H. et al.; "Relaxin: More Than Just a Hormone of Pregnancy"; *Elservier Science Publishers Ltd. (UK)*; 14:4–6 (1993).
Kibblewhite D. et al.; "The Effect of Relaxin on Tissue Expansion"; *Arch Otolaryngol Head Neck Surg*; 118:153–156 (1992).
MacLennan A.H. et al.; "Serum Relaxin in Pregnancy"; *The Lancet*; 241–245 (1986).
Ostgaard et al.; "Prevalence of Back Pain in Pregnancy"; *Spine*; 16:549–552 (1991).
Ostgaard et al.; "Previous Back Pain and Risk of Developing Back Pain in a Future Pregnancy"; *Spine*; 16:432–436 (1991).
Saugstad L.F.; "Persistent Pelvic Pain and Pelvic Joint Instability"; *European Journal of Obstetrics & Gynecology and Reproductive Biology*; 41:197–201 (1991).
Sherwood C.D. et al.; "Purification and Characterization of Porcine Relaxin"; *Academic Press, Inc.*; 160:185–196 (1974).
St–Louis J. et al.; "Chronic Disease of Blood Pressure by Rat Relaxin in Spontaneously Hypertensive Rats"; *Life Science*; 37–1351–1357 (1985).
Walsh J.R. et al.; "Use of an Octadecylsilica Purification Method Minimizes Proteolysis During Isolation of Porcine and Rat Relaxins"; *Endocrinology*; 107:1258–1260 (1980).

*Primary Examiner*—Cecilia J. Tsang
*Assistant Examiner*—P. Lynn Touzeau
*Attorney, Agent, or Firm*—Clark & Elbing LLP

[57] ABSTRACT

Disclosed is a method of reducing pain in a mammal involving administration of relaxin to the mammal.

9 Claims, No Drawings

USE OF RELAXIN AS AN ANALGESIC AND PALLIATIVE FOR INTRACTABLE PAIN

BACKGROUND OF THE INVENTION

This invention relates to the use of relaxin to reduce pain.

Relaxin is a peptide hormone primarily synthesized by the theca interna cells of the corpus luteum during pregnancy. It may also be synthesized in small amounts by the human uterus and placenta. It is known to cause relaxation of the pubic symphysis prior to parturition.

SUMMARY OF THE INVENTION

In general, the invention features a method of reducing pain in a mammal which involves administering relaxin to the mammal. In preferred embodiments, the mammal is a human; the pain is chronic; and the pain results from stretching, swelling, or dislocation of a tissue of the mammal (for example, chronic back pain, tumor pain, iatrogenic pain, arthritic joint pain, or postpartum pelvic joint pain).

Other features of the invention will be apparent from the following description of the preferred embodiments thereof, and from the claims.

DESCRIPTION OF THE PREFERRED EMBODIMENTS

Although relaxin may be used generally as an analgesic and palliative for pain, the conditions most amenable to its therapeutic administration are those in which unusual stress is chronically placed on tissues because of an acquired or inherent malformation which results in the displacement of tissues from their natural disposition in the body. Relaxin finds utility, for example, in the treatment of severe chronic pain, particularly pain arising from stretching, swelling, or dislocation of tissues. A partial list of preferred therapeutic indications follows; this list is provided to illustrate, not limit, the invention.

Chronic Back Pain

Chronic back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease. The first four of these causes of chronic back pain account for the great majority of cases, all of which are amenable to relaxin therapy.

Tumor Pain

The local unrestricted proliferation of cells in cancer leads to pain when the displaced tissues are subjected to the mechanical stress required to accommodate the increased volume occupied by the tumor mass. This pain has as its underlying cause the severe local stretching of tissues by the neoplastic lesion. When the tumor burden is confined to a small enclosed compartment, such as the marrow of a bone, the resulting pressure can result in severe pain which can be very difficult to manage clinically. Use of relaxin in the management of tumor pain will prove a valuable adjunct to more conventional, opioid-based therapies.

Iatrogenic Pain

Following invasive procedures or high dose radiation therapy, it is not uncommon for scar tissue to form which results in a debilitating compromise of freedom of motion and substantial chronic pain. Treatment with relaxin will reduce pain while also promoting the loosening of connective tissue structures.

Arthritic Joint Pain

The pain associated with osteoarthritis and rheumatoid arthritis appears to arise from local inflammation and the associated stimulation of nociceptive neurons. Administration of relaxin will substantially decrease the perception of painful stimuli in these conditions.

Postpartum Pelvic Joint Pain

In a small fraction of women, parturition precipitates chronic pain in the pelvis and pelvic joints. A correlation has been observed between women with high relaxin levels during pregnancy and the subsequent development of postpartum pelvic pain. Although the etiology of this pain is not understood, it is likely that it arises from a chronic intrapelvic tension similar to that found in lower back pain, and a return to the high relaxin levels experienced during pregnancy will palliate the symptomology.

THERAPY

Systemic Administration of Relaxin

For use as a pain reducer, relaxin may be administered systemically, for example, formulated in a pharmaceutically-acceptable buffer such as physiological saline. Preferable routes of administration include, for example, subcutaneous, intramuscular, or intradermal injections which provide continuous, sustained levels of the drug in the patient. In other preferred routes of administration, relaxin may be given to a patient by injection of a slow release preparation, slowly dissociating polymeric form, or crystalline form; this sort of sustained administration may follow an initial delivery of the drug by more conventional routes (for example, those described above). Alternatively, relaxin may be administered using an infusion pump, thus allowing a precise degree of control over the rate of drug release, or through instillation of relaxin in the nasal passages in a similar fashion to that used to promote absorption of insulin. Finally, as an alternative to nasal transmucosal absorption, relaxin may be delivered by aerosol deposition of a powder or solution into the lungs.

Local Administration of Relaxin

Relaxin may also be administered locally to achieve substantial palliative outcomes. Since the desired action of the agent is generally upon a circumscribed mass of tissue proximate to a specific stress, delivery of the hormone by means which promote high local concentrations in the vicinity of the stress may be especially desirable. For this reason injection of the agent into tissue sites adjacent to, or upstream of the draining circulation of the affected site will, where possible, be preferable. Alternatively, in conditions involving deep organ structures, for example in the displacement of tissue by invasive tumors, implantation near the affected site of sustained release formulations of relaxin (such as osmotic pumps or erodable polymeric compositions impregnated with the hormone) may be preferred.

Relaxin

Relaxin, for either systemic or local administration, may be obtained from any commercially available source (e.g., Genentech, Inc., South San Francisco, Calif.) or may be synthesized either by standard techniques of recombinant polypeptide production (see, e.g., Ausubel et al., *Current Protocols in Molecular Biology*, John Wiley & Sons, New York, 1989; Sambrook et al., *Molecular Cloning, A Laboratory Manual*, 2nd ed., Cold Spring Harbor Press, Cold Spring Harbor, N.Y., 1989) or by peptide synthesis (e.g., by the methods described in *Solid Phase Peptide Synthesis*, 2nd ed., 1984 The Pierce Chemical Co., Rockford, Ill.). Relaxin gene and peptide sequences are provided, e.g., in Hudson et al., Nature 301:628, 1983; Hudson et al., EMBO J. 3:2333, 1984; and Bryant-Greenwood, Molecular and Cellular Endocrinology 79:C125, 1991.

Generally, the relaxin polypeptide native to a species will be preferred for therapeutic administration. However, relaxin fragments or analogs shown to be functional, e.g., in the bioassays of Fei et al. (Biochem. Biophys. Res. Comm. 170:214–222, 1990) and Kramer et al. (In Vitro Cell. Dev. Biol. 26:647–656, 1990) are also useful in the invention. Particularly preferred relaxin fragments include the B29 relaxin fragment described by Winslow et al. (Proc. 71st Meeting of Endocrine Society 889 Abstract, 1989) and Bryant-Greenwood (supra). Particularly preferred relaxin analogs include polypeptides which differ from a native relaxin polypeptide only by conservative amino acid substitutions, for example, substitution of one amino acid for another of the same class (e.g., valine for glycine, arginine for lysine, aspartic acid for glutamic acid, etc.). Other preferred analogs include relaxin polypeptides which are modified for the purpose of increasing peptide stability; such analogs may contain, e.g., one or more desaturated peptide bonds or D-amino acids in the peptide sequence or may be formulated as cyclized peptide molecules. Finally, a prorelaxin polypeptide (see, e.g., Hudson et al., EMBO J. 3:2333, 1984; and Vu et al., Life Sci. 52:1055, 1993) may be administered as an analgesic and palliative for pain according to the invention.

Dosage

Relaxin is administered systemically at a dosage that provides reduction in pain, typically between 0.1–1.6 nanogram/ml and preferably 0.7 nanogram/ml. Where local administration schemes are employed, the concentrations of relaxin in the affected tissue may substantially exceed these levels.

Because administration of the relaxin polypeptide may promote loosening of connective tissues, it may be desirable, where possible, to encourage muscular development through physical therapy to counteract any excessive loosening observed during the course of relaxin treatment.

OTHER EMBODIMENTS

The methods of the invention may be used to reduce the disorders described herein in any mammal, for example, humans, domestic pets, or livestock. Where a non-human mammal is treated, the relaxin employed is preferably specific for that species (see, e.g., Haley et al., DNA 1:155, 1982).

Other embodiments are within the following claims.

We claim:

1. A method of reducing pain which results from stretching, swelling, or dislocation of a tissue in a mammal, comprising administering a pain-reducing amount of relaxin to said mammal.

2. The method of claim 1, wherein said mammal is a human.

3. The method of claim 1, wherein said pain is chronic.

4. The method of claim 1, wherein said pain is chronic back pain.

5. The method of claim 1, wherein said pain is tumor pain.

6. The method of claim 1, wherein said pain is iatrogenic pain.

7. The method of claim 1, wherein said pain is arthritic joint pain.

8. The method of claim 1, wherein said pain is postpartum pelvic joint pain.

9. The method of claims 1 or 2, wherein said relaxin is human relaxin.

* * * * *